United States Patent
Elkin et al.

(10) Patent No.: US 9,040,040 B2
(45) Date of Patent: May 26, 2015

(54) ENZYME COMBINATIONS TO REDUCE BRAIN TISSUE SWELLING

(71) Applicant: The Trustees of Columbia University in the City of New York, New York, NY (US)

(72) Inventors: Benjamin Simon Elkin, Toronto (CA); Barclay Morrison, III, New York, NY (US); John Desmond Finan, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/900,755

(22) Filed: May 23, 2013

(65) Prior Publication Data
US 2013/0259848 A1    Oct. 3, 2013

Related U.S. Application Data

(63) Continuation-in-part of application No. PCT/US2011/061858, filed on Nov. 22, 2011.

(60) Provisional application No. 61/416,440, filed on Nov. 23, 2010.

(51) Int. Cl.
*A61K 38/46* (2006.01)
*A61K 38/47* (2006.01)
*A61K 38/51* (2006.01)
*A61K 38/54* (2006.01)

(52) U.S. Cl.
CPC ............... *A61K 38/54* (2013.01); *A61K 38/47* (2013.01); *A61K 38/46* (2013.01); *A61K 38/465* (2013.01); *A61K 38/51* (2013.01)

(58) Field of Classification Search
CPC ....... A61K 38/54; A61K 38/51; A61K 38/46; A61K 38/465; A61K 38/47
See application file for complete search history.

(56) References Cited

U.S. PATENT DOCUMENTS 7,612,032 B2 * 11/2009 Genkin et al. ................. 514/1.1
2006/0198820 A1 * 9/2006 McDonald et al. .......... 424/85.1

FOREIGN PATENT DOCUMENTS

WO    WO 2006035445 A2 *    4/2006

OTHER PUBLICATIONS

Elkin ("Chondroitin Sulfate Proteoglycans Contributed to Brain Tissue Swelling Behavior" Proceedings of th 2010 IEEE 36th Annual Northeast, Mar. 26-28, 2010).*

* cited by examiner

*Primary Examiner* — Blaine Lankford
*Assistant Examiner* — Charles Zoltan Constantine
(74) *Attorney, Agent, or Firm* — Law Offices of Albert Wai-Kit Chan, PLLC

(57) ABSTRACT

Tissue fixed charge density (FCD) is identified as another potential therapeutic target for reducing brain tissue swelling. Reduction of the FCD could reduce the thermodynamic force driving water entry into the brain. The present invention discloses chondroitinase ABC (ChABC) reduces tissue FCD and reduces tissue swelling, indicating that it may be an effective treatment to reduce edema and control intracranial pressure.

5 Claims, 8 Drawing Sheets

ENZYME COMBINATIONS TO REDUCE BRAIN TISSUE SWELLING

CROSS-REFERENCE TO RELATED APPLICATIONS

This application is a Continuation-in-part of Int'l App'l No. PCT/US2011/061858, filed Nov. 22, 2011, which claims priority of U.S. application No. 61/416,440, filed Nov. 23, 2010. The entire contents and disclosures of the preceding applications are incorporated by reference into this application.

FIELD OF THE INVENTION

This invention relates to neurology, specifically regarding swelling of the brain. The invention discloses a method of treating Increased Intracranial Pressure (ICP) due to edema following severe traumatic brain injury (TBI) by reducing the fixed charge density (FCD) of brain tissue.

BACKGROUND OF THE INVENTION

Current acute treatments for the severely head-injured patient are focused on management of increased intracranial pressure (ICP) as a result of edema. Malignant ICP is a strong indicator for poor outcome, and its treatment is one of the most effective means of reducing mortality and morbidity (Ghajar, 2000; Treggiari et al., 2007). Treatment strategies for reducing ICP generally focus on the use of osmotic agents such as mannitol (Rangel-Castilla et al., 2008) or more recently hypertonic saline (Kerwin et al., 2009). The efficacy of mannitol however has been called into question recently (Wakai et al., 2007).

The search for new therapeutic targets continues with much attention devoted to two main areas: aquaporin channels and breakdown of the blood brain barrier (BBB) (Amorini et al., 2003; Vink and van den Heuvel, 2010; Zador et al., 2007). These components of the central nervous system represent major routes of entry for water into the brain during edema and act as facilitators to brain tissue swelling. One of the main drivers of brain tissue swelling is the fixed negative charge within brain cells that draws water into the brain following injury according to the Donnan effect (Elkin et al., 2010b).

The Donnan effect describes the tendency for a hydrated material comprised of charged molecules to generate an osmotic gradient of ions between its interstitium and the bathing solution due to the material's affinity for soluble and oppositely charged ions. This osmotic gradient produces a Donnan osmotic pressure, p, according to the following equation (Overbeek, 1956):

$$p = RT(\sqrt{(c^F)^2 + (\bar{c}^*)^2} - \bar{c}^*) \quad (1)$$

where R is the ideal gas constant, is absolute temperature, $c^*$ is the bath osmolarity, and $c^F$ is the concentration of the charged molecules fixed within the material known as the fixed charge density (FCD). The Donnan osmotic pressure will increase if the FCD increases or if the bath osmolarity decreases. Due to the osmotic pressure difference, water may be drawn into the material until the interstitial fluid pressure is balanced by tension in the solid matrix (due to its expansion) according to triphasic mixture material principles (Lai et al., 1991).

Negative charges on cytoplasmic constituents affect the ion balance between cells and the extracellular fluid (ECF) based on the Donnan effect (Kurbel, 2008). The homeostatic state requires both electroneutrality (with a negative membrane potential) and osmotic balance. This balance is maintained by multiple ion channels and pumps in the cell membrane, including the ATP-dependent Na+/K+ pump. Following injury, metabolic disruption compromises this homeostasis, resulting in exposure of the FCD to the ECF and an increase of the Donnan osmotic pressure inside cells. As ions enter cells, Donnan-mediated cellular swelling occurs, leading to the progression of edema as described in FIG. 1 and described in more detail in the discussion.

SUMMARY OF THE INVENTION

The present invention provides a treatment for brain edema by altering the FCD. The present invention also provides methods for altering FCD. Furthermore, the said methods may be used to treat brain edema. In one embodiment of this invention, the brain behaves as a triphasic mixture material once this FCD is exposed. Triphasic mixture theory has been used to describe mechanical and swelling behavior of cartilage in which the fixed charge density is mostly composed of sulfated glycosaminoglycan (GAG) chains such as those that make up chondroitin sulfate proteoglycans (CSPGs) (Sun et al., 2004). Brain also contains a significant amount of CSPGs as well as heparin sulfate proteoglycans (HSPGs) (Margolis et al., 1975). The braids high DNA content, which also has negatively charged phosphate groups at physiologic pH (Kurbel, 2008), was also investigated as a potential source of FCD. The effect of enzymes that degrade these molecules on the swelling behavior of dead and living brain tissue was examined. Degradation of all FCD candidates resulted in significant reduction in tissue swelling. Chondroitinase ABC, which digests CSPGs, was most effective at reducing brain tissue swelling behavior and could represent a new therapeutic strategy for reducing edema following injury.

1. In the homeostatic, healthy state, water flux across the BBB (J) is governed by Starling's relation which takes into account BBB permeability to water, vascular and tissue hydrostatic and osmotic pressures, and the reflection coefficient for solutes (ions, proteins, etc.) (Kimmelberg, 2004; Rapoport, 1978). Cell ion homeostasis is maintained by ATP-dependent Na+/K+ pumps along with other ion pumps and channels (Kurbel, 2008).

2. Following injury, cell metabolism is disrupted and the ability to maintain the resting membrane potential and transcellular ion gradients is lost.

3. Cations rush into cells to balance the FCD. Increased cation concentration relative to the ECF increases the osmotic potential in the cell resulting in water influx, cellular swelling, and subsequent compaction of the extracellular space.

4. Rate of tissue swelling is increased by breakdown of the BBB that can occur after swelling-induced release of inflammatory factors, increasing the rate of ion and water influx into the tissue (Donkin and Vink, 2010).

5. As cells continue to swell and die, more FCD will be exposed, and the Donnan osmotic pressure will continue to increase, thereby driving ICP above cerebral perfusion pressure (CPP). Further ischemic damage will ensue.

Figure 1:
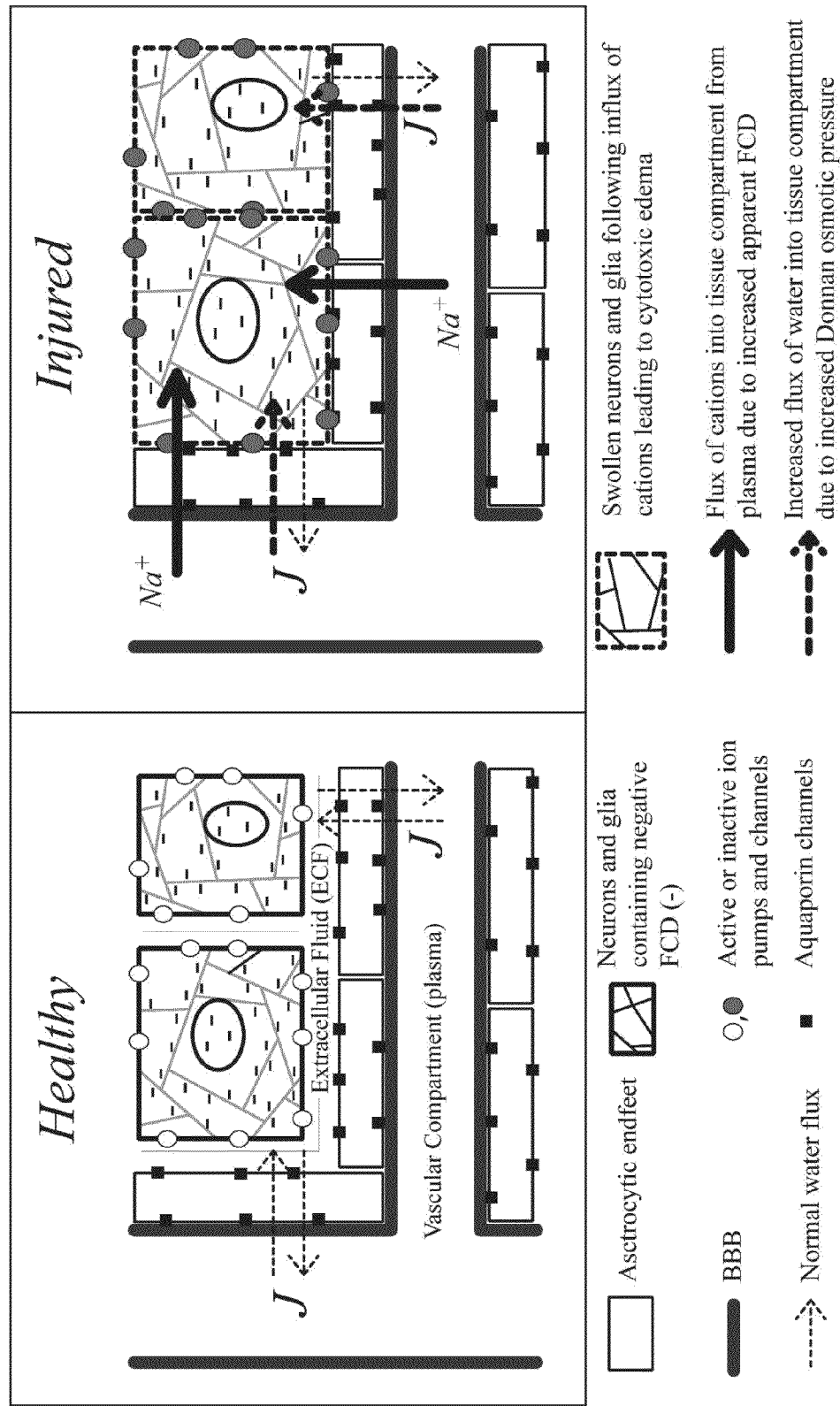
FIG. 1 is a schematic presentation of the proposed mechanisms of edema and the effect of fixed charge density (FCD) on tissue swelling.
Figure 2:
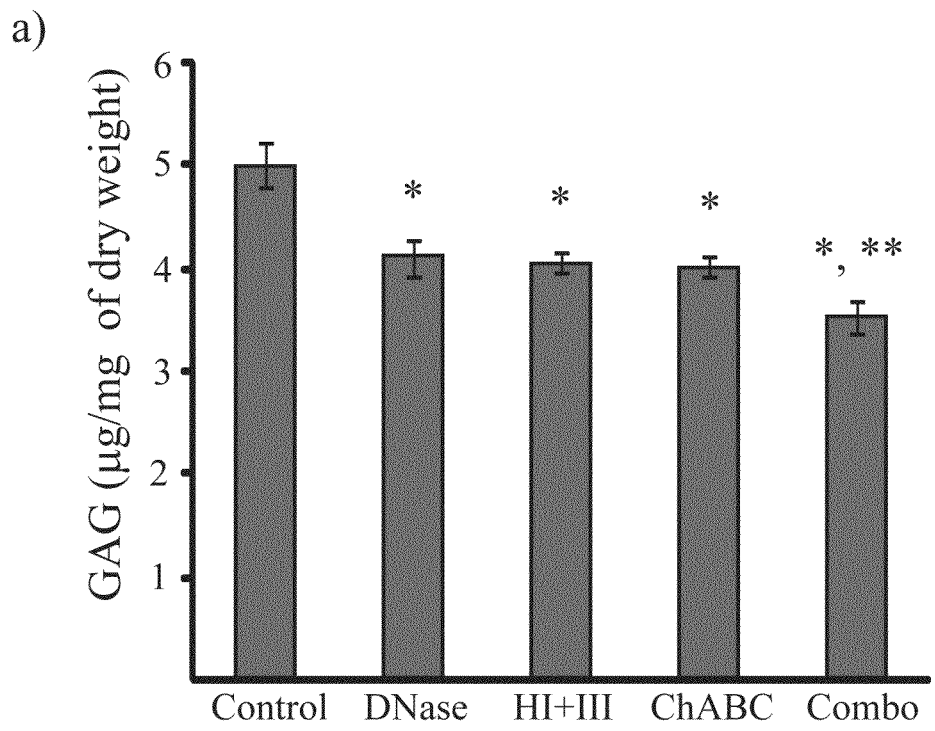
Figure 2:
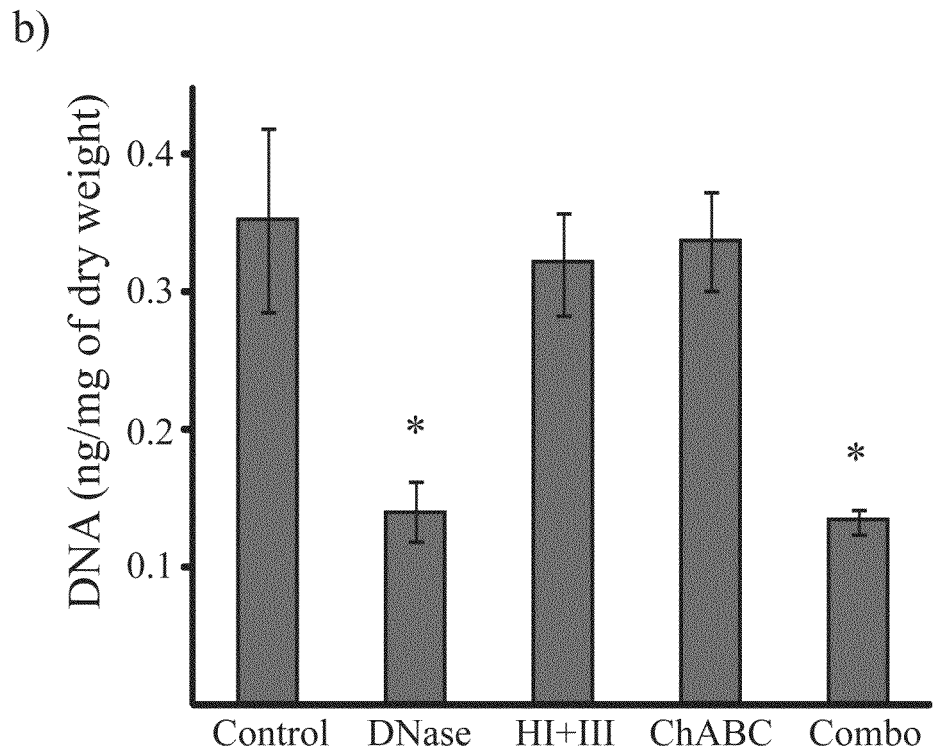

FIG. 2 shows Glycosaminoglycan content as measured by a DMMB assay (a) and DNA content (B) in tissue after 24 h treatment with single enzymes (DNase, HI+III, ChABC) or in combination (Combo). (mean±s.e.m.; *, p<0.05 compared to controls; **, p<0.05 compared to single enzyme treatments)

Figure 3:
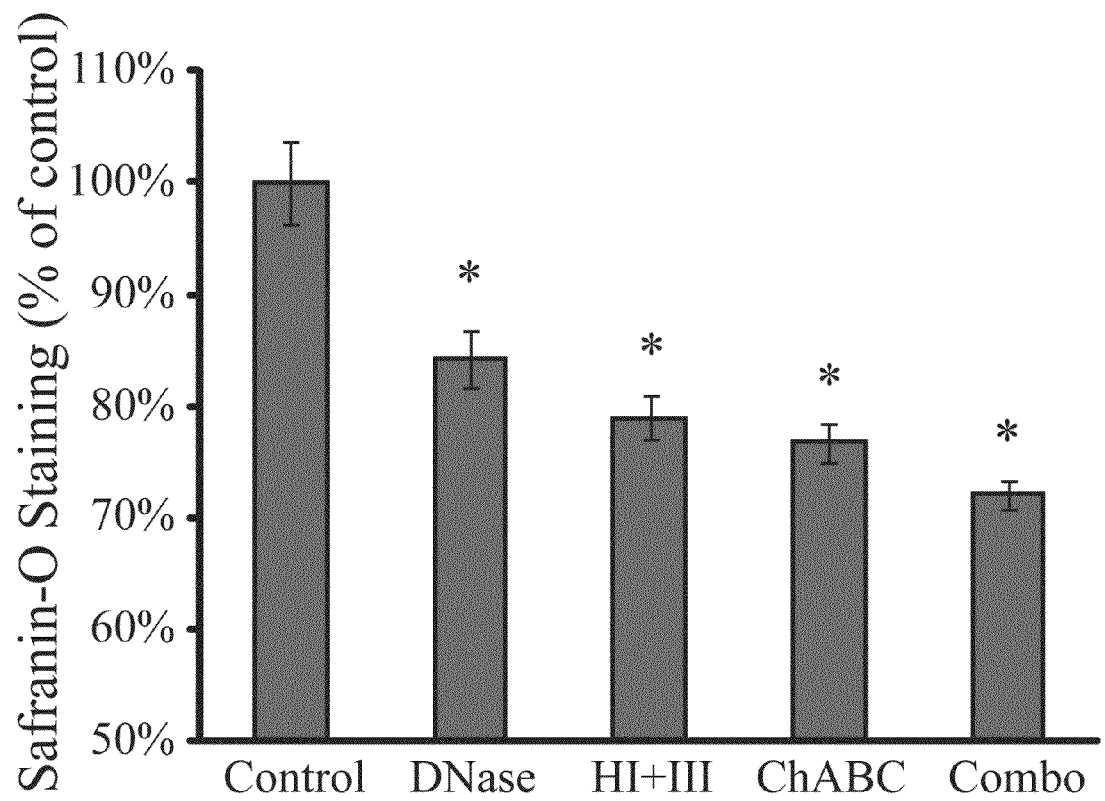

FIG. 3 shows the average optical density of Safranin-O stained sections of tissue after 24 h treatment with single enzymes (DNase, HI+III, ChABC) or in combination (Combo). (mean±s.e.m.; *, p<0.01 compared to controls)

Figure 4:
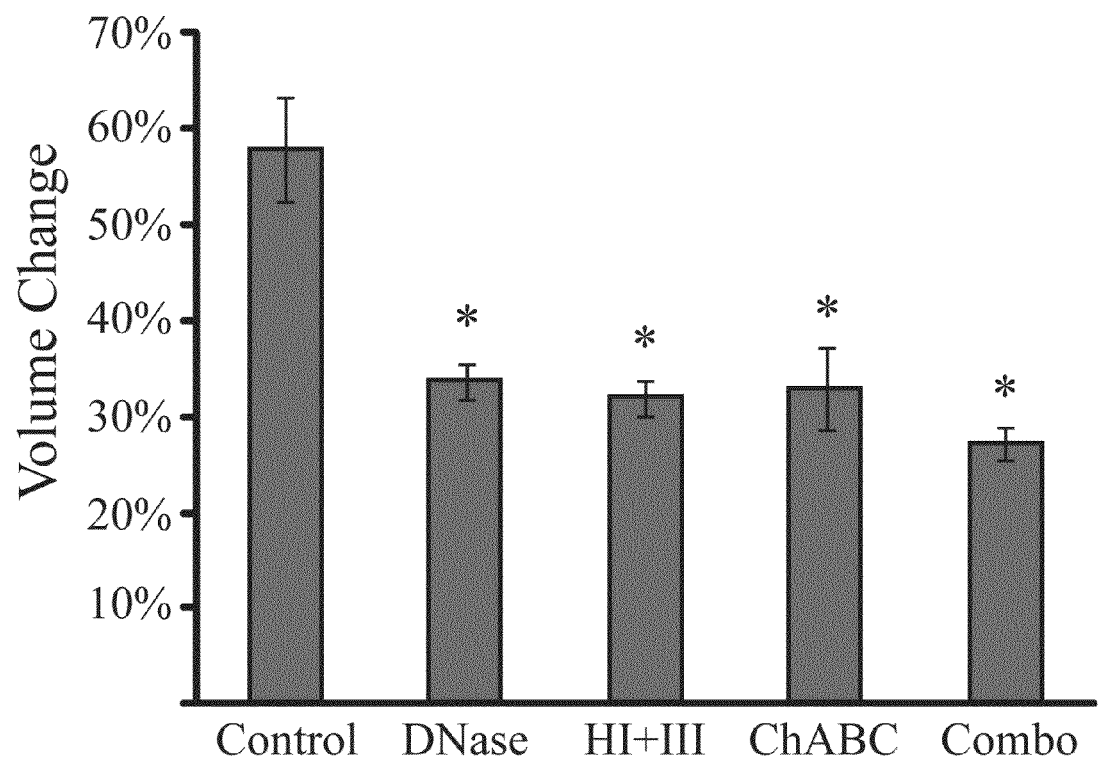

FIG. 4 shows the change in tissue slice volume after 24 h treatment with single enzymes (DNase, HI+III, ChABC) or in combination (Combo). (mean±s.e.m.; *, p<0.01 compared to controls)

Figure 5:
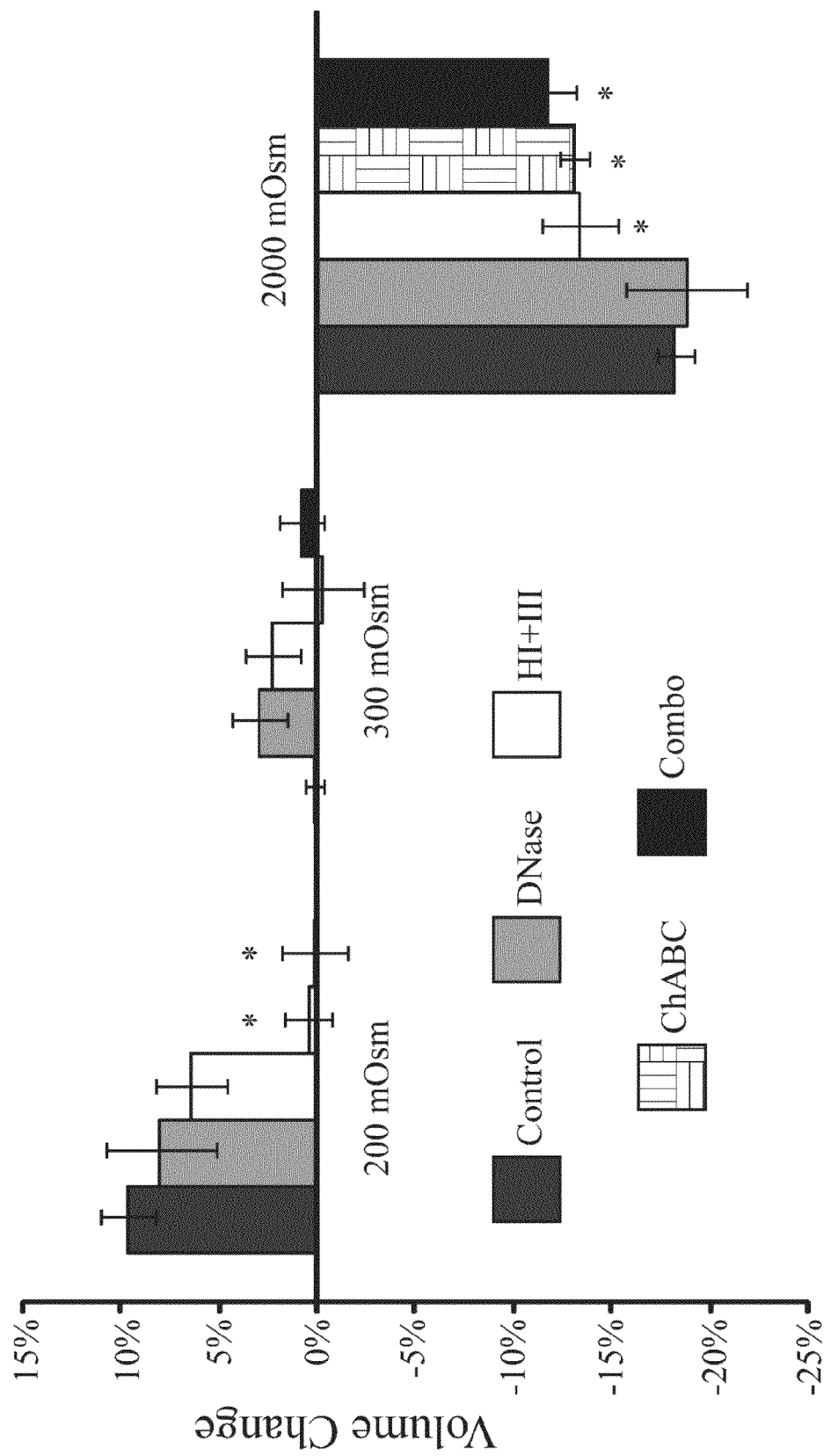

FIG. 5 shows the change in slice volume after 3 h incubation in hypotonic (200 mOsm), isotonic (300 mOsm), and hypertonic (2000 mOsm) bathing solutions. (mean±s.e.m.; *, p<0.05 compared to controls)

Figure 6:
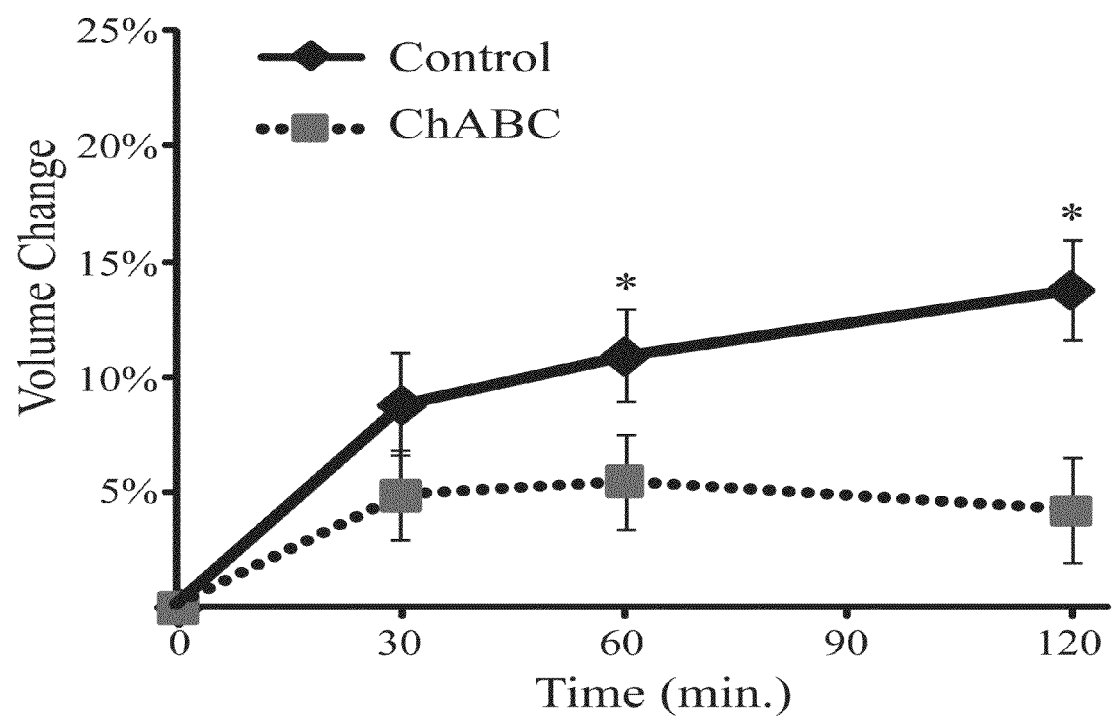

FIG. 6 shows the effect of ChABC treatment on the swelling behavior of live tissue. (mean±s.e.m.; *,p<0.05 within time point)

Figure 7:
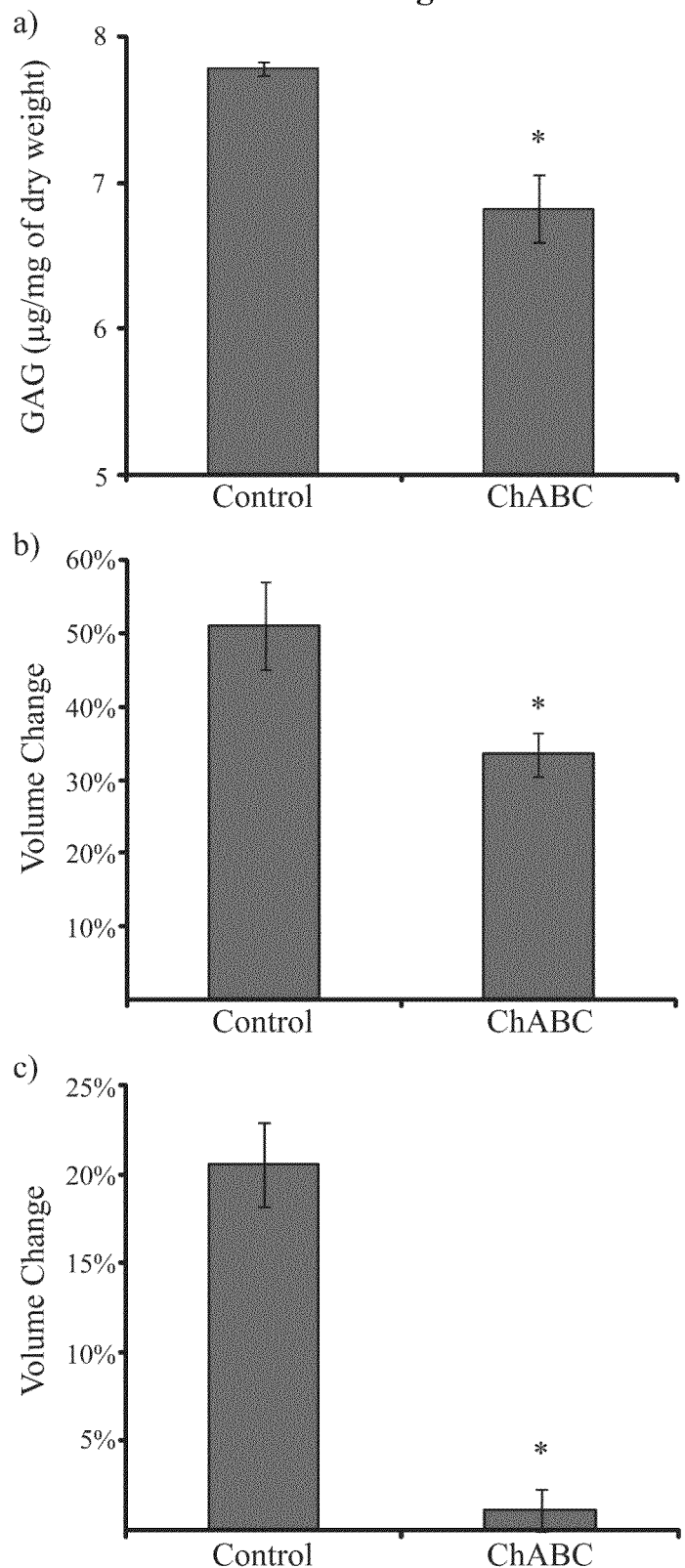

FIG. 7 shows the Effect of ChABC treatment on glycosaminoglycan content (A), 24 h swelling (B), and volume change after 3 h incubation in hypotonic (200 mOsm) bathing solution (C) for slices of the porcine cortex. (mean±s.e.m.; *, p<0.05)

Figure 8:
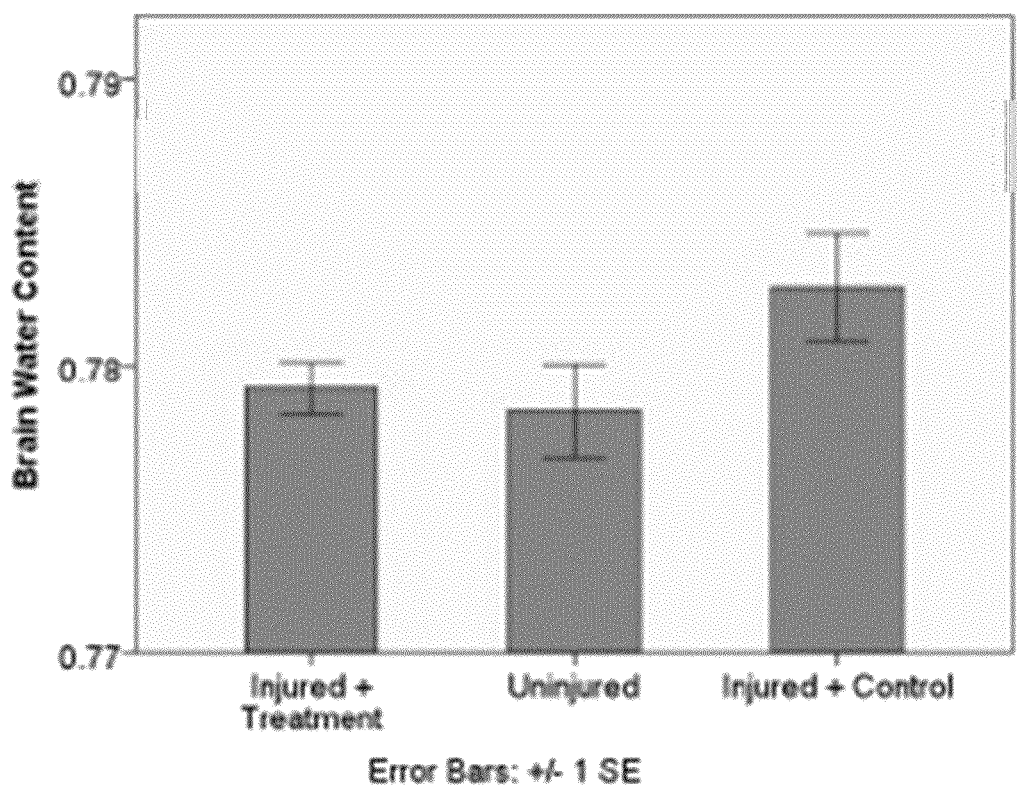

FIG. 8 shows water fraction in mouse brain samples (n=6, mean±s.e.m.). In injured mice, brains were harvested 24 hours after injury. The treatment was chondroitinase ABC injected into the injury site immediately after injury. The control was penicillinase injected into the injury site immediately after injury. Uninjured mice received neither enzyme.

DETAILED DESCRIPTION OF THE INVENTION

The fundamental requirement of the Donnan effect is that a mixture material, in this case cells within the brain, contain negatively charged molecules that are fixed within the material. These molecules make up the FCD and contain negatively charged side groups which have high affinity for soluble cations such as Na+ and K+. The osmotic pressure generated by the resultant osmolarity gradient, as described by Equation 1, draws water into the material as it expands to reduce the density of fixed charges and the associated higher ionic content/osmolarity compared to the bathing fluid. A mixture material that can expand without restriction will in effect reduce the osmotic pressure to zero. However, if the material resists expansion either due to its stiffness in dilatation or due to confinement in a rigid container, its internal pressure will rise according to Equation 1. In the case of the brain inside the skull, the ICP will increase.

After brain injuries such as TBI or stroke the FCD within cells is exposed to the extracellular compartment, and a new Donnan equilibrium will be achieved. Tissue osmolarity is increased following injury in the focal and penumbral areas (Kawamata et al., 2007). This increase in osmolarity is capable of generating large pressures on the order of tens of mmHg Increased osmolarity is likely a result of repartitioning of ions into the tissue from the vascular compartment as previously observed even in models in which the BBB remains impermeable to large molecules (Young et al., 1986; Young et al., 1987). The vascular compartment acts as a source of ions and water for the swelling brain. The low elastic modulus of brain (Elkin et al., 2010a; Gefen et al., 2003), especially in tension (Miller and Chinzei, 2002), cannot resist the osmotic pressure from driving expansion. Expansion continues until the rigid cranial vault prevents further swelling. ICP then increases and continues to increase as more cells become affected and more FCD becomes exposed, increasing the osmotic pressure in the tissue according to Equation 1.

The Donnan effect has also been used to describe ion distributions in cells and body fluid compartments (Nguyen and Kurtz, 2006), and may be one of the driving forces behind cytotoxic swelling. Cytotoxic swelling has been considered the dominant contributor to edema following injury (Marmarou et al., 2006b). Indirect measurements have shown that persistent edema is manifested through cytotoxic swelling with either transient or no BBB opening (Marmarou et al., 2006a). There are many causes of cytotoxic swelling that can be triggered by injury including metabolic breakdown, depolarization, increased extracellular K+, glutamate excitotoxicity, oxidative stress, membrane damage, and ion overload (Pasantes-Morales and Cruz-Rangel, 2009). However, the mechanism driving the cell swelling has not been fully described. It is known that intra- and extracellular ion distribution may be predicted by the Donnan effect which is mediated both by intracellular protein charges and active pumping of sodium and other ions out of the cell (Kurbel, 2008; Simard et al., 2007). However, when the cell membrane is compromised, the thermodynamic potential comprised of the external cations and internal negative FCD is dissipated, resulting in an influx of water, swelling of the FCD, and hence cytotoxic edema (Tomita et al., 1988; Tomita and Gotoh, 1992). Cytotoxic swelling may therefore be due to the osmotic pressure generated following exposure of negatively charged molecules that are physically fixed within cells. Tissue swelling in vitro can be accelerated following disruption of the plasma membrane or metabolic inhibition (Elkin et al., 2010b), but that the ultimate degree of swelling at equilibrium is unchanged.

Another often-encountered hypothesis to explain cytotoxic edema is simple discharge of the transmembrane potential and associated equilibration of Na+ and K+ gradients. In the absence of an FCD however, dissipation of the transmembrane voltage would not necessarily result in water uptake as intra- and extracellular ion concentrations would be equal. In a cell containing an FCD, the ultimate concentration of cations will be higher within the damaged cell due to their attraction to the negatively charged FCD. The initial pressurization due to the Donnan effect easily swells the cell due to its low modulus of elasticity (Lu et al., 2006), reducing the effective FCD and resulting in a swollen cell at ionic equilibrium with its surrounding environment. During in vitro studies of cell metabolism disruption or inhibition, intracellular Na+ and K+ concentrations have been found to equilibrate with the bathing medium (Silver et al., 1997).

Computational models of cytotoxic edema also predict that membrane voltage goes to zero but only with a concomitant increase in cell volume (Dronne et al., 2006). These findings are consistent with an FCD required within cells for the generation of cell swelling following metabolic breakdown. The effect of enzyme treatment on candidate molecular species that may contribute to the intracellular FCD exposed following injury was examined. The candidates include chondroitin sulfate proteoglycans (CSPGs), heparin sulfate proteoglycans (HSPGs), and DNA. CSPGs and HSPGs contain sulfate side groups that possess strong negative charges at physiological pH. They are expressed throughout the brain at all stages of development (Jenkins and Bachelard, 1988), predominantly within the cellular cytoplasm in adult brain tissue (Aquino et al., 1984; Margolis et al., 1979), as well as integrated with the cell membrane in perineuronal nets (Deepa et al., 2006). DNA is also present throughout the brain due to its high cellular content. Phosphate groups attached to each nucleotide are negatively charged at physiologic pH. The intracellular localization and strong negative charge of these molecules make them likely candidates contributing to cellular FCD. The enzymes used here for digesting specific brain glycosaminoglycan chains included chondroitinase ABC (ChABC) and heparinase I+III (HI+III), which have been used by others to digest CSPGs and HSPGs from brain tissue (Papageorgakopoulou et al., 2001). These enzymes were capable of decreasing FCD as measured by both the DMMB assay (FIG. 2a) and Safranin-O staining (FIG. 3). DNase I (DNase) is a commonly used enzyme for digesting single-stranded DNA, double-stranded DNA and chromatin. In the current study, DNase reduced the DNA content in tissue slices by approximately 60% (FIG. 2b) while ChABC and HI+III had no significant effect on DNA content. Interestingly, while each enzyme alone was capable of decreasing FCD content by approximately 20% (FIGS. 2a and 3), the effect of all three enzymes was not additive and reduced the FCD by only 30% according to the DMMB assay and 28% according to Safranin-O staining. Possible reasons could include interactions of the enzymes that reduce activity, poor access of the enzymes to their substrates, or poor diffusion of digested molecules out of the tissue. The inability of enzymes alone or in combination to decrease FCD by more than 30% suggests that additional negatively charged molecules comprise the FCD that are not removed with ChABC, HI+III, or DNAse treatment. These negatively charged molecules can include cytoskeletal and other structural proteins as well as other intracellular protein complexes. There are also other glycosaminoglycans such as keratan sulfate proteoglycans that are present but in a smaller concentration than CSPGs and HSPGs (Papageorgakopoulou et al., 2001). Complete digestion of the tissue's FCD may not be possible and may not be desirable. Significant reductions in FCD following enzymatic treatment however suggests that all three molecules could contribute to swelling according to the Donnan equation. Consequently, a reduction of FCD (cF) will decrease the Donnan osmotic pressure subsequent to exposure of the remaining intracellular FCD according to Equation 1. As expected, following digestion and incubation for 24 h, each enzyme similarly reduced tissue swelling by almost half as compared to controls (FIG. 4). To verify that changes in tissue swelling following enzyme treatment were due to a reduction in FCD, the effect of changing the bath ionic osmolarity (c*) on tissue swelling was tested. According to Equation 1, if enzyme treatment did indeed decrease cF, then changes in c* would have less of an effect on tissue volume change. Controls behaved as expected, swelling with a decrease in bath osmolarity (c*) and decreasing in volume with an increase in c*.

While ChABC- and HI+III-treated slices exhibited similar changes in FCD and initial swelling, their triphasic swelling behaviors were slightly different. HI+III-treated slices swelled in response to hypotonic bathing solution although less so than controls. In contrast, ChABC treated slices did not swell in response to hypotonic bathing solution (FIG. 5). Both groups however responded in a similar manner to the hypertonic bathing solution, decreasing in volume significantly less than controls. These differences suggest that ChABC may be more effective in reducing the FCD that contributes to Donnan osmotic swelling. In addition, the combination of all enzymes did not have a significantly larger effect on tissue swelling behavior compared to ChABC alone (FIG. 5). Injection of ChABC into the brain immediately after controlled cortical impact injury reduced brain tissue water content measured 24 h after injury (FIG. 8).

ChABC may therefore represent a potential therapeutic treatment for malignant brain edema following severe injury. Its direct application may be most feasible in cases of large necrotic regions or mass lesions that require surgical evacuation (Kawamata and Katayama, 2006).

ChABC could be used to replace or to accompany neurosurgical evacuation of the lesion with the goal of reducing the FCD in the lesion area, thereby reducing the Donnan osmotic pressure, ultimately lowering ICP. In support of this proposed therapy, ChABC treatment of live slices of rat cortex resulted in an almost immediate reduction in slice swelling following dissection (FIG. 6). The initial swelling (0-30 min) is possibly due to the cells cut on the surfaces of the slice during dissection.

The ChABC could quickly digest the FCD in these cells as well as the extracellular CSPGs which contribute to the FCD of live tissue. Slice volume is maintained at a lower volume than untreated controls for the first 2 h following dissection which suggests that ChABC may be an effective treatment for dealing with both acute and chronic edema following injury. ChABC has traditionally been viewed as a facilitator of neural regeneration following injury since CSPGs generated by reactive astrocytes are believed to inhibit neural regrowth and plasticity (Galtrey and Fawcett, 2007; Sherman and Back, 2008). Following injury, CSPGs are upregulated (Asher et al., 2000; McKeon et al., 1999) and may contribute to increased tissue FCD following less severe injury without necrosis or exposure of intracellular FCD. ChABC may therefore have the dual effect of reducing tissue FCD and creating an environment permissive to regeneration, which may explain its beneficial effects as a treatment in a rat model of injury (Lin et al., 2008).

Interestingly, DNase-treated slices did not behave differently than controls (FIG. 5) which suggests that the initial reduction in tissue swelling for these slices may not be due to FCD that is active in Donnan osmotic pressurization. These results also suggest that the phosphate groups of DNA may not contribute to the Donnan osmotic pressure to the same degree as GAGs. One possibility is that since cell bodies make up much of the tissue in the gray matter of the cortex, it is possible that digestion of DNA can be accompanied by structural instability of the cell nucleus which could lead to a slight decrease in cell volume. DNase I is also known to bind filamentous actin and cause its depolymerization (Hitchcock, 1980). The breakdown of this major component of the solid matrix that makes up brain tissue could have an effect on initial swelling and the resistance to swelling during osmotic challenge.

To determine whether similar mechanisms of swelling were present in the brains of larger mammals, slices of porcine parietal cortex were subjected to ChABC treatment and a similar set of tests were performed (FIG. 7). ChABC significantly reduced FCD, initial tissue swelling, and swelling in response to hypotonic bathing solution of pig brain tissue. There was little species variation in outcomes except for the larger FCD content in porcine brain and increased swelling in response to incubation in hypotonic solution. The increased FCD content and lower elastic modulus of porcine brain tissue relative to rat tissue (Gefen et al., 2003; Gefen and Margulies, 2004) could explain these differences. Since ChABC treatment was effective at reducing swelling for both species, it may have similar effects on human brain.

Brain swelling requires both a route of entry and a driving force for water to flow into the brain (Kimelberg, 2004; Rapoport, 1978). Breakdown of the BBB coupled with an increase in accessible FCD will result in immediate and sustained tissue swelling. Recent evidence has suggested that inflammatory factors released by brain cells following injury such as kinins and tachykinins contribute to increased BBB permeability to water and small molecules including soluble ions (Donkin and Vink, 2010). Treatment strategies directed at controlling BBB permeability and cell membrane permeability could reduce the rate of water entry into the brain following injury, allowing extant, albeit compromised, and volume regulation mechanisms to counter ion and water influx. Here, we have identified tissue FCD as another potential therapeutic target.

Reduction of the FCD could reduce the thermodynamic force driving water entry into the brain. In one embodiment of the invention, the ChABC reduces tissue FCD and reduces tissue swelling. Future in vivo studies on the progression and treatment of edema may benefit from the direct injection of ChABC into the injury site to control edema, as demonstrated in FIG. 8. In view of the data presented herein, one of ordinary skill in the art would readily utilize these data and apply them to animal models or clinical settings to determine various parameters such as dosage, route of administration etc.

In one embodiment, the present invention provides a use of a composition for the preparation of medicament for reducing brain tissue swelling, said composition comprising enzymes that reduce fixed charge density of the brain tissue. For example, the composition comprises enzymes that digest chondroitin sulfate proteoglycans or heparin sulfate proteoglycans. In one embodiment, the enzyme that digests chondroitin sulfate proteoglycans is chondroitinase ABC. In another embodiment, the enzyme that digests heparin sulfate proteoglycans is heparinase, such as heparinase I and heparinase III. In yet another embodiment, the composition may further comprise enzyme that digests DNA, such as DNase I.

The present invention also provides a method of reducing brain tissue swelling, comprising the step of contacting the brain tissue with a composition comprising enzymes that reduce fixed charge density of the brain tissue. For example, the composition comprises enzymes that digest chondroitin sulfate proteoglycans or heparin sulfate proteoglycans. In one embodiment, the enzyme that digests chondroitin sulfate proteoglycans is chondroitinase ABC. In another embodiment, the enzyme that digests heparin sulfate proteoglycans is heparinase, such as heparinase I and heparinase III. In yet another embodiment, the composition may further comprise enzyme that digests DNA, such as DNase I.

The present invention also provides a method of reducing brain tissue swelling in a subject, comprising the step of administering to the subject a composition comprising enzymes that reduce fixed charge density of the brain tissue. For example, the composition comprises enzymes that digest chondroitin sulfate proteoglycans or heparin sulfate proteoglycans. In one embodiment, the enzyme that digests chondroitin sulfate proteoglycans is chondroitinase ABC. In another embodiment, the enzyme that digests heparin sulfate proteoglycans is heparinase, such as heparinase I and heparinase III. In yet another embodiment, the composition may further comprise enzyme that digests DNA, such as DNase I.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

EXAMPLE 1

Materials and Methods

Tissue Preparation

All animal procedures were approved by the Columbia University Institutional Animal Care andUse Committee (IACUC). For rat studies, brains were rapidly removed from adult Sprague Dawley rats (~280 g) and placed in a cooled dish. For porcine studies, brains from adult Yorkshire pigs (~50 kg) were received immediately following sacrifice after use in other studies unrelated to the brain and brought to the laboratory for dissection within 1 h of sacrifice. For both species, strips of cortical tissue were dissected, and 350 µm thick slices were generated on a McIlwain tissue chopper (Harvard Apparatus). Rectangular sections (approximate dimensions: 3×1.5×0.35 mm) were created by removing white matter and meninges leaving only cortical grey matter. Slices were placed in Gey's salt solution supplemented with 10 mM D-glucose (Sigma) until used.

Enzyme Digestion

Slices were separated into dishes containing Gey's salt solution alone (Control) or supplemented with either X units/ml chondroitinase ABC (ChABC), X units/ml heparinase I and heparinase III (HI+III), X units/ml DNase I (DNase), or a combination of all four enzymes (Combo). For 24 h swelling and osmotic challenge experiments, dishes were first placed on an orbital shaker for 2 h to facilitate enzyme diffusion into the tissue and then incubated for 22 h at 37° C. Dishes were also supplemented with 5 mM sodium cyanide and 10 mM 2-deoxyglucose to generate conditions of maximal cytotoxic swelling over the 24 h incubation period according to the previous study (Elkin et al., 2010b). For live slice imaging, no sodium cyanide or 2-deoxyglucose was added, and dishes were bubbled vigorously with oxygen and maintained at 37° C. for the full 2 h of the experiment.

Biochemical Assays

Tissue slices for biochemical assays were weighed wet before being dried overnight in an oven at 75° C. Dry tissue was weighed and then digested overnight at 37° C. in papain digest buffer (0.1 M sodium acetate buffer, pH 5, containing 5 mM EDTA, 5 mM cysteine HCl and 2 U papain ml-i; Farndale et al. 1982). Glycosaminoglycan (GAG) content was then measured with a standard 1,9 dimethylmethylene blue (DMMB) assay and expressed as µg per mg of dry tissue. DNA content was measured using a PicoGreen assay kit (Invitrogen) and expressed as ng of DNA per mg of dry tissue.

Safranin-O Staining and Quantitative Densitometry

Tissue slices for Safranin-O staining were fixed for 1 h at room temperature in 4% formaldehyde in PBS (Sigma). After serial dehydration in ethanol, slices were embedded in paraffin and sectioned at 20 µm and mounted onto slides. Sections were then dewaxed, rehydrated, stained in 0.1% Safranin-O (Sigma) for 2 h, destained in tap water for 5 mM, dehydrated and coverslipped with Permount (Sigma). Bright-field images were acquired on an inverted microscope (Olympus IX71) using Kohler illumination at 20× magnification. Quantitative densitometry was performed by converting the gray-scale image (IMAGE) to an optical density using the following equation:

$$OpticalDensity = -\text{Log}_{10}\left(\frac{IMAGE - BACKGROUND}{SHADING}\right) \quad (2)$$

BACKGROUND and SHADING represent images used to correct for camera black level and uneven illumination, respectively. Average gray level of the OpticalDensity was recorded for the entire image.

Volume Measurement

As described previously (Elkin et al., 2010b), volume measurements were performed on an inverted microscope (Olympus IX71) outfitted with fiber-optic side-lighting and a custom-built mirrored reflector placed at a 45° angle relative to the bottom of the dish (FIG. 2). The image projected to the objective consisted of orthogonal views of both the slice area and thickness simultaneously. Light transmission images were captured at 4× magnification, and volume was calculated as the product of area and average thickness of the slice. Slice volume was measured immediately following dissection. Following 24 h incubation, volume was measured again and expressed as a percentage change from initial volume. The 24 h volume was also used as the baseline for ionic osmolarity challenge on dead slices.

For the osmotic challenge experiment, the bathing solution was changed to either hypotonic (300 mOsm Gey's salt solution diluted to 200 mOsm with ddH2O), isotonic (300 mOsm Gey's salt solution) or hypertonic solutions (300 mOsm Gey's salt solution supplemented with NaCl to 2000 mOsm) and placed on an orbital shaker for 3 h. Osmolarity of bathing solutions was verified with a freezing point osmometer (Advanced Instruments, Inc.). Volume was again measured and expressed as a percentage change from initial volume (volume measured at 24 h following dissection). For live slice experiments, two groups of slices (Control and ChABC) were imaged immediately following dissection and at 30, 60, and 120 min following dissection. Volume change was expressed as a percent change from the initial volume, as above.

Treatment of Post-Traumatic Edema in Mice

All procedures for experiments on animals were approved by the Columbia University Institutional Animal Care and Use Committee. C57/BL6 mice were given 0.1 mg/kg buprenorphine for analgesia and anesthetized with 4% isoflurane by inhalation. Mice were then mounted in a stereotactic frame and supplied with 2% isoflurane by inhalation to maintain anesthesia. The skull was exposed and a 5 mm diameter cranectomy was created in the skull between lambda and bregma on the left side of the sagittal suture using a dental drill. A commercial controlled cortical impactor system (Impact One, Leica Biosystems, Buffalo, Ill.) was used to injure the brain. This system includes a electromagnetically actuated, cylindrical steel indenter 3 mm in diameter. The indenter was positioned in contact with the exposed surface of the cortex and then indented into the brain to a depth of 1 mm at a speed of 4.4 m/s and held at this position for 300 ms before retraction. Thereafter, 3 µl of enzyme solution was injected into the brain at the injury site at a rate of 1 µl/min using a Hamilton syringe (Hamilton Company, Reno, Nev.). The treatment enzyme was chondroitinase ABC (Sigma Aldrich, St. Louis, Mo.) and the control enzyme was penicillinase (Sigma Aldrich, St. Louis, Mo). Immediately after treatment, the scalp was sutured and the mouse was removed from anesthesia and placed in a recovery cage.

All animals were euthanized 24 hours after injury. The brains were removed immediately after death. A 4 mm thick coronal slab containing the injury site was cut from the brain and weighed to determine its wet weight. Thereafter, it was placed in an oven at 95 degrees for 72 hours. The sample was then weighed again and the wet and dry weights were compared to determine the fraction of the initial wet weight that was water.

Statistics

All statistical analyses were performed using SPSS (SPSS, Inc.). One-way ANOVA was used to examine the effect of enzyme treatment on FCD content from DMMB assays, DNA content, FCD content in Safranin-O stained sections, and change in slice volume after 24 h incubation. In all four studies, Bonferroni post hoc tests were performed on treatment type. For osmotic challenge studies, a two-way ANOVA was performed on treatment group and osmolarity to examine the effect of enzyme treatment on the change in slice volume after 3 h incubation in solutions of different ionic osmolarity. Bonferonni post hoc tests were performed on treatment type within each osmolarity group. For live tissue swelling studies, a two-way ANOVA was performed to examine the effect of time and treatment on change in volume. Bonferroni post hoc tests were performed on time. A t-test was then performed at each time point to determine the effect ChABC treatment on change in volume. For porcine tissue studies, t-tests were performed to examine the effect of ChABC treatment on FCD content, initial 24 h tissue swelling, and swelling in response to incubation in hypotonic bathing solution. For all statistical tests, a p-value of less than 0.05 was considered statistically significant.

EXAMPLE 2

Results

The effect of 24 h enzyme treatment on the GAG fixed charge as measured by the DMMB assay is shown in FIG. 2a. Values are expressed as percentage of dry weight of the tissue to normalize for differences in tissue water content based on amount of swelling (Elkin et al., 2010b). DNase, HI+III, and ChAB C treatment all significantly reduced GAG content as compared to controls. The combination of enzymes (Combo group) significantly reduced GAG content as compared to each enzyme alone and controls; however the combined effect was not additive. DNA content was significantly reduced by more than half in DNase and Combo groups (FIG. 2b) and was not significantly different than controls in HI+III and ChABC groups.

The effect of enzyme treatment on FCD was verified by staining thin sections of enzymeterated slices of tissue with the cationic dye Safranin-O. Optical density was used as a measure of dye intensity, and average optical density as a percent of controls for each treatment group is shown in FIG. 3. DNase, HI+III, ChABC, and Combo treatment all significantly decreased Safranin-O staining relative to controls (16%, 21%, 23%, and 28% respectively).

These data correlate well with the results of the DMMB assay above and verify that all treatments were capable of reducing FCD. The change in tissue volume after 24 h incubations at 37° C. and the effect of enzyme treatment is presented in FIG. 4. Undigested, control slices increased in volume by about 60% over 24 h. All enzyme treatment groups swelled significantly less than controls, increasing in volume by about half of controls. There were no significant differences between the different enzyme treatments.

The effect of a reduction in FCD on triphasic swelling behavior of enzyme-treated and untreated dead tissue was measured following exposure to solutions of different ionic osmolarities (FIG. 5). As expected, control slices swelled in hypotonic solution, did not change volume in isotonic solution, and decreased in volume in hypertonic solutions. DNase-treated slices behaved similarly to controls (p=1). ChABC- and Combo-treated tissue did not swell in hypotonic solutions, did not change volume in isotonic solution, and decreased volume significantly less than controls and DNase-treated slices. HI+III-treated slices swelled in hypotonic solution, did not significantly change volume in isotonic solution, and decreased volume by the same amount as ChABC- and Combo-treated slices.

The effect of ChABC treatment on live tissue was examined by measuring the volume change of oxygenated and glucose supplemented slices maintained at 37° C. at 30, 60, and 120 min following dissection (FIG. 6). At all-time points, ChABC treated slices swelled significantly less than controls by about half as much. Following initial swelling (0-30 min) for both ChABC treated and control slices; there was no significant change in volume over the following two intervals (30-60 and 60-120 min.)

To determine whether CSPGs contribute to tissue swelling in the same manner in a larger animal model as they do in rat, the effect of ChABC treatment on slices of porcine cortex was examined. Total GAG content in control slices was higher in porcine versus rat control slices (0.78% versus 0.50%), and GAG content was significantly reduced in ChABC-treated porcine slices to 0.68% (FIG. 7a). Control slices swelled about 52%, and ChABC-treated slices swelled only 33% (FIG. 7b). Incubation of dead tissue for 3 h in hypotonic solution swelled controls by 20% but did not swell ChABC-treated slices. Differences between ChABC treated and control slices of porcine cortex were significant for all tests.

Treatment with ChABC reduced brain edema after traumatic brain injury in mice. In injured mice treated with a control enzyme, the water fraction was 0.7826 (S.D.=0.0052, n=6). In injured mice treated with chondroitinase ABC, the water fraction was 0.7793 (S.D.=0.0038, n =6). The average water fraction for uninjured and untreated mice is 0.7784. Therefore, ChABC treatment eliminated approximately 75% of the swelling due to injury.

REFERENCES

Amorini A M, Dunbar J G and Marmarou A. (2003). Modulation of aquaporin-4 water transport in a model of TBI. Acta Neurochir Suppl. 86:261-263.

Aquino D A, Margolis R U and Margolis R K. (1984) Immunocytochemical localization of a chondroitin sulfate proteoglycan in nervous tissue. I. Adult brain, retina, and peripheral nerve. J Cell Biol. 99:1117-1129.

Asher R A, Morgenstern D A, Fidler P S, Adcock K H, Oohira A, Braistead J E, Levine J M, Margolis R U, Rogers J H and Fawcett J W. (2000). Neurocan is upregulated in injured brain and in cytokine-treated astrocytes. J. Neurosci. 20:2427-2438.

Deepa S S, Carulli D, Galtrey C, Rhodes K, Fukuda J, Mikami T, Sugahara K and Fawcett J W. (2006). Composition of perineuronal net extracellular matrix in rat brain: a different disaccharide composition for the net-associated proteoglycans. J. Biol.Chem. 281:17789-17800.

Donkin J J and Vink R. (2010). Mechanisms of cerebral edema in traumatic brain injury: therapeutic developments. Curr Opin Neurol.

Dronne M A, Boissel J P and Grenier E. (2006). A mathematical model of ion movements in grey matter during a stroke. J Theor Biol. 240:599-615.

Elkin B S, Ilankovan A and Morrison B. (2010a). Age-Dependent Regional Mechanical Properties of the Rat Hippocampus and Cortex. J Biomech Eng. 121.

Elkin B S, Shaik M A and Morrison B, 3rd. (2010b). Fixed negative charge and the Donnan effect: a description of the driving forces associated with brain tissue swelling and oedema. Philos Transact A Math Phys Eng Sci. 368:585-603.

Galtrey C M and Fawcett J W. (2007). The role of chondroitin sulfate proteoglycans in regeneration and plasticity in the central nervous system. Brain Res Rev. 54:1-18.

Gefen A, Gefen N, Zhu Q L, Raghupathi R and Margulies S S. (2003). Age-dependent changes in material properties of the brain and braincase of the rat. Journal of Neurotrauma. 20:1163-1177.

Gefen A and Margulies S S. (2004). Are in vivo and in situ brain tissues mechanically similar? Journal of Biomechanics. 37:1339-1352.

Ghajar J. (2000). Traumatic brain injury. Lancet. 356:923-929.

Hitchcock S E. (1980). Actin deoxyroboncuclease I interaction. Depolymerization and nucleotide exchange. J Biol Chem. 255:5668-5673.

Jenkins H G and Bachelard H S. (1988). Developmental and age-related changes in rat brain glycosaminoglycans. J Neurochem. 51:1634-1640.

Kawamata T and Katayama Y. (2006). Surgical management of early massive edema caused by cerebral contusion in head trauma patients. Acta Neurochir. Suppl. 96:3-6.

Kawamata T, Mori T, Sato S and Katayama Y. (2007). Tissue hyperosmolality and brain edema in cerebral contusion. Neurosurg.Focus. 22:E5-.

Kerwin A J, Schinco M A, Tepas J J, 3rd, Renfro W H, Vitarbo E A and Muehlberger M. (2009). The use of 23.4% hypertonic saline for the management of elevated intracranial pressure in patients with severe traumatic brain injury: a pilot study. J Trauma. 67:277-282.

Kimelberg H K. (2004). Water homeostasis in the brain: basic concepts. Neuroscience. 129:851-860.

Kurbel S. (2008). Are extracellular osmolality and sodium concentration determined by Donnan effects of intracellular protein charges and of pumped sodium? J Theor Biol. 252:769-772.

Lai W M, Hou J S and Mow V C. (1991). A triphasic theory for the swelling and deformation behaviors of articular cartilage. J Biomech Eng. 113:245-258.

Lin R, Kwok J C, Crespo D and Fawcett J W. (2008). Chondroitinase ABC has a long-lasting effect on chondroitin sulphate glycosaminoglycan content in the injured rat brain. J Neurochem. 104:400-408.

Lu Y B, Franze K, Seifert G, Steinhauser C, Kirchhoff F, Wolburg H, Guck J, Janmey P, Wei E Q, Kas J and Reichenbach A. (2006). Viscoelastic properties of individual glial cells and neurons in the CNS. Proc. Natl. Acad. Sci. U.S.A. 103:17759-17764.

Margolis R K, Thomas M D, Crockett C P and Margolis R U. (1979). Presence of chondroitin sulfate in the neuronal cytoplasm. Proc Natl Acad Sci USA. 76:1711-1715.

Margolis R U, Margolis R K, Chang L B and Preti C. (1975). Glycosaminoglycans of brain during development. Biochemistry. 14:85-88.

Marmarou A, Signoretti S, Aygok G, Fatouros P and Portella G. (2006a). Traumatic brain edema in diffuse and focal injury: cellular or vasogenic? Acta Neurochir Suppl. 96:24-29.

Marmarou A, Signoretti S, Fatouros P P, Portella G, Aygok G A and Bullock M R. (2006b). Predominance of cellular edema in traumatic brain swelling in patients with severe head injuries.

J Neurosurg. 104:720-730. McKeon R J, Jurynec M J and Buck C R. (1999). The chondroitin sulfate proteoglycans neurocan and phosphacan are expressed by reactive astrocytes in the chronic CNS glial scar. J.Neurosci. 19:10778-10788.

Miller K and Chinzei K. (2002). Mechanical properties of brain tissue in tension. Journal of Biomechanics. 35:483-490.

Nguyen M K and Kurtz I. (2006). Quantitative interrelationship between Gibbs-Donnan equilibrium, osmolality of body fluid compartments, and plasma water sodium concentration. J Appl Physiol. 100:1293-1300.

Overbeek J T. (1956). The Donnan equilibrium. Prog Biophys Biophys Chem. 6:57-84.

Papageorgakopoulou N, Theocharis A D, Skandalis S S, Vynios D H, Theocharis D A and Tsiganos C P. (2001). Keratan sulphate in cerebrum, cerebellum and brainstem of sheep brain. Biochimie 83:973-978.

Pasantes-Morales H and Cruz-Rangel S. (2009). Brain volume regulation: osmolytes and aquaporin perspectives. Neuroscience.

Rangel-Castilla L, Gopinath S and Robertson C S. (2008). Management of intracranial hypertension. Neurol Clin. 26:521-541, x.

Rapoport S I. (1978). A mathematical model for vasogenic brain edema. J Theor Biol. 74:439-467.

Sherman L S and Back S A. (2008). A 'GAG' reflex prevents repair of the damaged CNS. Trends Neurosci. 31:44-52.

Silver I A, Deas J and Erecinska M. (1997). Ion homeostasis in brain cells: differences in intracellular ion responses to energy limitation between cultured neurons and glial cells. Neuroscience. 78:589-601.

Simard J M, Kent T A, Chen M, Tarasov K V and Gerzanich V. (2007). Brain oedema in focal ischaemia: molecular pathophysiology and theoretical implications. Lancet Neurol. 6:258-268.

Sun D D, Guo X E, Likhitpanichkul M, Lai W M and Mow V C. (2004). The influence of the fixed negative charges on mechanical and electrical behaviors of articular cartilage under unconfined compression. J Biomech Eng. 126:6-16.

Tomita M and Gotoh F. (1992). Cascade of cell swelling: thermodynamic potential discharge of brain cells after membrane injury. Am J Physiol. 262:H603-610.

Tomita M, Gotoh F and Kobari M. (1988). Colloid osmotic pressure of cat brain homogenate separated from autogenous CSF by a copper ferrocyanide membrane. Brain Res. 474:165-173.

Treggiari M M, Schutz N, Yanez N D and Romand J A. (2007). Role of intracranial pressure values and patterns in predicting outcome in traumatic brain injury: a systematic review. Neurocrit Care. 6:104-112.

Vink R and van den Heuvel C. (2010). Substance P antagonists as a therapeutic approach to improving outcome following traumatic brain injury. Neurotherapeutics. 7:74-80.

Wakai A, Roberts I and Schierhout G. (2007). Mannitol for acute traumatic brain injury. Cochrane Database Syst Rev.CD001049.

Young W, DeCrescito V, Flamm E S, Hadani M, Rappaport H and Cornu P. (1986). Tissue Na, K, and Ca changes in regional cerebral ischemia: their measurement and interpretation. Cent Nery Syst Trauma. 3:215-234.

Young W, Rappaport Z H, Chalif D J and Flamm E S. (1987). Regional brain sodium, potassium, and water changes in the rat middle cerebral artery occlusion model of ischemia. Stroke. 18:751- 759.

Zador Z, Bloch O, Yao X and Manley G T. (2007). Aquaporins: role in cerebral edema and brain water balance. Prog Brain Res. 161:185-194.

What is claimed is:

1. A method of reducing brain tissue swelling in a subject in need thereof, comprising the step of administering to the subject a composition comprising an enzyme that digests chondroitin sulfate proteoglycans, an enzyme that digests heparin sulfate proteoglycans, and an enzyme that digests DNA.

2. The method of claim 1, wherein the enzyme that digests chondroitin sulfate proteoglycans is chondroitinase ABC.

3. The method of claim 1, wherein the enzyme that digests heparin sulfate proteoglycans is heparinase.

4. The method of claim 3, wherein the heparinase is heparinase I or heparinase III.

5. The method of claim 1, wherein the enzyme that digests DNA is DNase I.

* * * * *